United States Patent
Lin et al.

(10) Patent No.: US 10,012,646 B2
(45) Date of Patent: Jul. 3, 2018

(54) SENSING CHIP

(71) Applicant: Industrial Technology Research Institute, Hsinchu (TW)

(72) Inventors: Ding-Zheng Lin, Taipei (TW); Feng-Sheng Kao, Hsinchu (TW); Ting-Yu Shih, Taipei (TW); Ping-Chen Chen, Taipei (TW); Jen-You Chu, Hsinchu (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 147 days.

(21) Appl. No.: 14/983,568

(22) Filed: Dec. 30, 2015

(65) Prior Publication Data

US 2017/0184584 A1    Jun. 29, 2017

(30) Foreign Application Priority Data

Dec. 24, 2015    (TW) .............................. 104143507 A

(51) Int. Cl.
*G01N 21/75* (2006.01)
*G01N 33/543* (2006.01)
*G01N 33/553* (2006.01)

(52) U.S. Cl.
CPC . *G01N 33/54393* (2013.01); *G01N 33/54353* (2013.01); *G01N 33/54373* (2013.01); *G01N 33/553* (2013.01)

(58) Field of Classification Search
CPC ....... G01N 33/54393; G01N 33/54373; G01N 33/54353; G01N 33/553
See application file for complete search history.

(56) References Cited

U.S. PATENT DOCUMENTS

| 8,071,391 B2 | 12/2011 | Rubinstein et al. |
| 8,426,152 B2 | 4/2013 | Gerion et al. |
| 8,508,744 B2 | 8/2013 | Valsesia et al. |

(Continued)

FOREIGN PATENT DOCUMENTS

| CN | 103335984 | 10/2013 |
| CN | 102764677 | 4/2014 |

(Continued)

OTHER PUBLICATIONS

Bellapadrona et al, "Optimization of Localized Surface Plasmon Resonance Transducers for Studying Carbohydrate-Protein Interactions" Anal. Chem. 2012, 84, 232-240.*

(Continued)

*Primary Examiner* — Dennis White
(74) *Attorney, Agent, or Firm* — Birch, Stewart, Kolasch & Birch, LLP

(57) ABSTRACT

A sensing chip including a substrate, a plurality of metal nanostructures, a first surface modified layer and a second surface modified layer is provided. The metal nanostructures are disposed on the substrate. The first surface modified layer is disposed on a surface of the metal nanostructures, wherein the first surface modified layer includes a plurality of thiol group-containing molecules. The second surface modified layer is disposed on a surface of the substrate, wherein the second surface modified layer includes a plurality of silyl group-containing molecules.

13 Claims, 10 Drawing Sheets

(56) References Cited

U.S. PATENT DOCUMENTS

| | | | |
|---|---|---|---|
| 8,514,398 | B2 | 8/2013 | Pang et al. |
| 8,529,988 | B2 | 9/2013 | Rubinstein et al. |
| 8,592,226 | B2 | 11/2013 | Van Duyne et al. |
| 8,663,554 | B2 | 3/2014 | Lin et al. |
| 9,012,207 | B2 | 4/2015 | Blair et al. |
| 9,091,683 | B2 | 7/2015 | Lin et al. |
| 2009/0257062 | A1 | 10/2009 | Rubinstein et al. |
| 2010/0041566 | A1 | 2/2010 | Zhang et al. |
| 2012/0188551 | A1 | 7/2012 | Langhammar et al. |
| 2014/0204372 | A1 | 7/2014 | Pang et al. |
| 2016/0282341 | A1* | 9/2016 | Singamaneni ......... B82Y 15/00 |

FOREIGN PATENT DOCUMENTS

| | | |
|---|---|---|
| CN | 104076013 | 10/2014 |
| CN | 104076021 A | 10/2014 |
| CN | 104246480 | 12/2014 |
| TW | 201142289 A1 | 12/2011 |
| TW | I404930 | 8/2013 |
| TW | M488629 | 10/2014 |
| TW | I485388 B | 5/2015 |
| TW | 201546437 A | 12/2015 |

OTHER PUBLICATIONS

Shen et al, "Plasmonic gold mushroom arrays with refractive index sensing figures of merit approaching the theoretical limit" Nat. Commun. Aug 27, 2013, 4 1102-10.*

Saito et al, "Novel Gold-Capped Nanopillars Imprinted on a Polymer Film for Highly Sensitive Plasmonic Biosensing" Anal. Chem. 2012, 84, 5494-5500.*

Shen et al., "Plasmonic gold mushroom arrays with refractive index sensing figures of merit approaching the theoretical limit," Nature Communications, Aug. 27, 2013, pp. 1-9.

Otte et al., "Improved Biosensing Capability with Novel Suspended Nanodisks," The Journal of Physical Chemistry C, Mar. 4, 2011, pp. 5344-5351.

Haes et al., "A nanoscale optical biosensor: sensitivity and selectivity of an approach based on the localized surface plasmon resonance spectroscopy of triangular silver nanoparticles," Journal of the American Chemical Society, Aug. 8, 2002, pp. 10596-10604.

Veiseh et al., "Highly Selective Protein Patterning on Gold-Silicon Substrates for Biosensor Applications," American Chemical Society, Jul. 26, 2002, pp. 6671-6678.

Marie et al., "Generic surface modification strategy for sensing applications based on Au/SiO2 nanostructures," Biointerphases, Mar. 29, 2007, pp. 49-54.

Feuz et al., "Improving the Limit of Detection of Nanoscale Sensors by Directed Binding to High-Sensitivity Areas," ACS Nano, Apr. 8, 2010, pp. 2167-2177.

Herzer et al., "Fabrication of patterned silane based self-assembled monolayers by photolithography and surface reactions on silicon-oxide substrates," Chemical Communications, Jul. 28, 2010, pp. 5634-5652.

Cinel et al., "Electron beam lithography designed silver nano-disks used as label free nano-biosensors based on localized surface plasmon resonance," Optics express, Jan. 30, 2012, pp. 2587-2597.

Cao et al, "Gold nanorod-based localized surface plasmon resonance biosensors: A review," Sensors and Actuators B: Chemical, May 2014, pp. 332-351.

Chen et al., "Optimization and Application of Reflective LSPR Optical Fiber Biosensors Based on Silver Nanoparticles," Sensors, May 26, 2015, pp. 12205-12217.

Veiseh et al, "Single-cell-based sensors and synchrotron FTIR spectroscopy: a hybrid system towards bacterial detection," Biosens Bioelectron, Apr. 27, 2007, pp. 253-260.

* cited by examiner

SENSING CHIP

CROSS-REFERENCE TO RELATED APPLICATION

This application claims the priority benefit of Taiwan application serial no. 104143507, filed on Dec. 24, 2015. The entirety of the above-mentioned patent application is hereby incorporated by reference herein and made a part of this specification.

TECHNICAL FIELD

The disclosure relates to a chip, and in particular, to a sensing chip.

BACKGROUND

Localized surface plasmon resonance (LSPR) technology is a testing method without fluorescent labeling. Other than shortening the testing process and testing time, this method does not cause a problem that the secondary antibody (containing fluorescent molecules) is difficultly conjugated due to steric hindrance. However, the sensitivity level of the current LSPR chip is lower as compared with the sensitivity level of the traditional ELISA method. Besides the reason that the plasmon resonance spectrum is wider, the main key is whether the analyte molecule is able to be close to the position of a sensing hot spot on the metal nanostructure so as to generate the effective spectral shift. Therefore, how to effectively conjugate the analyte molecule onto the metal nanostructures becomes an important issue that the researchers are eager to solve.

SUMMARY

Accordingly, the disclosure is directed to a sensing chip, wherein the sensing chip has a high sensitivity level and a strong linear relationship corresponding to a concentration of analyte molecules.

The disclosure provides a sensing chip including a substrate, a plurality of metal nanostructures, a first surface modified layer and a second surface modified layer. The metal nanostructure is disposed on the substrate. The first surface modified layer is disposed on the surface of the metal nanostructure, wherein the first surface modified layer includes a plurality of thiol group-containing molecules. The second surface modified layer is disposed on the surface of the substrate, wherein the second surface modified layer includes a plurality of silyl group-containing molecules.

Based on the above, in the disclosure, the metal nanostructures and the substrate of the sensing chip are spaced apart by a distance, so that the sensing hot spot is shifted upward from the substrate and is exposed, thereby having a higher sensitivity level. In addition, the sensing chip of the disclosure undergoes the two-stages surface modification, which not only increases the probability that the analyte molecules being conjugated on the effective sensing area, but also reduces the noise interference generated by the analyte molecules sticking on the non-sensing area, thereby enhancing the linear relationship between the signal strength and the concentrations of the analyte molecules, and increasing sensitivity level of the sensing chip.

In order to make the aforementioned and other features and advantages of the disclosure more comprehensible, several exemplary embodiments accompanying figures are described in details.

DETAILED DESCRIPTION OF DISCLOSED EMBODIMENTS

FIGS. 1A to 1F are schematic cross-sectional views depicting a manufacturing process of a sensing chip according to a first embodiment of the disclosure. Firstly, a substrate 100 is provided, and the substrate 100 is a glass substrate, for example. A photoresist layer 110 and a patterned mask layer 120 located on the photoresist layer 110 were formed on the substrate 100. In the present embodiment, the photoresist layer 110 is an organic photoresist layer, and the patterned mask layer 120 is a patterned inorganic photoresist layer. A method of forming the patterned mask layer 120 is, for example, forming an inorganic resist layer on the photoresist layer 110, and making the inorganic resist layer undergo a phase-change by a blue ray laser thermal lithography process, so as to pattern the inorganic resist layer. The patterned mask layer 120 has a plurality of openings 122, and the openings 122 exposes a portion of the photoresist layer 110. In the present embodiment, an area exposed by the openings 122 is used to define a predetermined region of metal nanostructures.

Figure 1A:
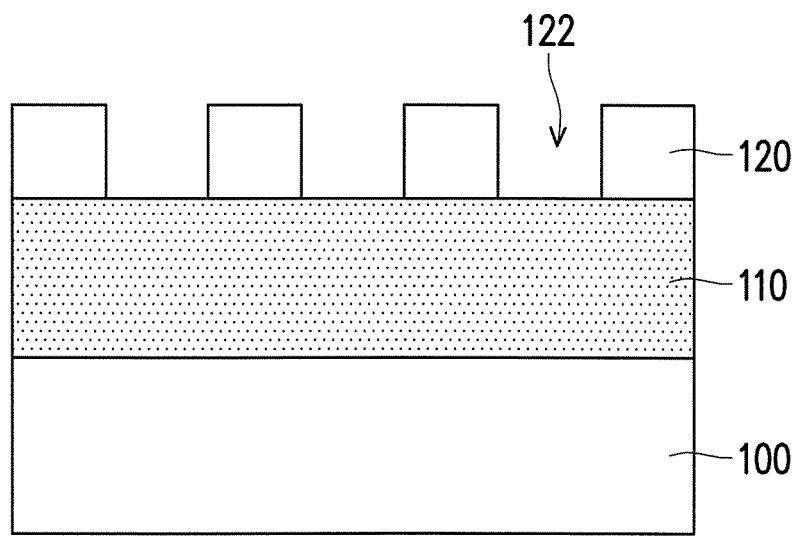
FIGS. 1A to 1F are schematic cross-sectional views depicting a manufacturing process of a sensing chip according to a first embodiment of the disclosure.
Figure 1B:
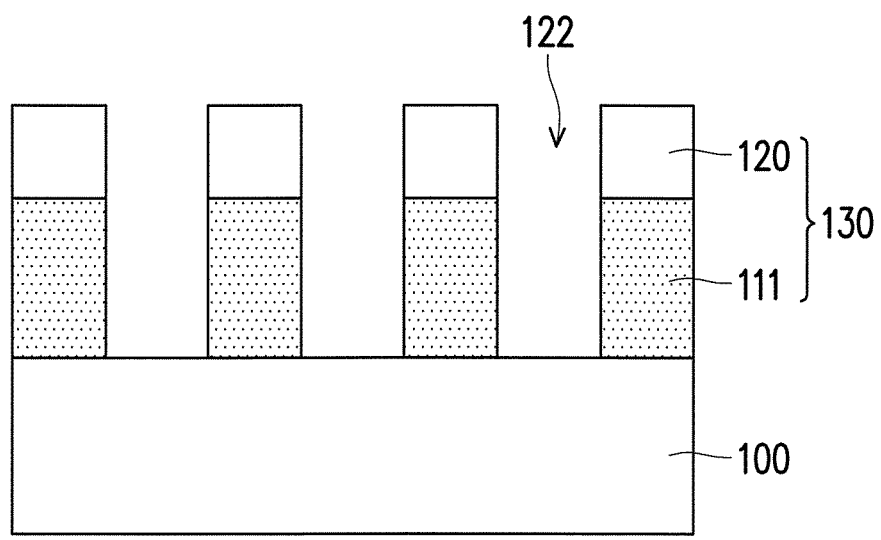

Subsequently, referring to FIG. 1B, the patterned mask layer 120 serves as an etching mask, and an etching process is performed to remove the portion of the photoresist layer 110 exposed by the openings 122, so as to form a plurality of stacking structures 130 that are separated from each other. The etching process may be an isotropic dry etching process or an anisotropic dry etching process. The isotropic dry etching process is reactive ion etching (RIE), for example. The anisotropic dry etching process is, for example, inductively coupled plasma etching (ICP). Each of the stacking structure 130 includes a patterned photoresist layer 111 and the patterned mask layer 120 disposed on the patterned photoresist layer 111. In this step, a pattern of the patterned mask layer 120 is transferred to the patterned photoresist layer 111. In other words, a positioning configuration of the pattern of the patterned photoresist layer 111 approximately corresponds to a positioning configuration of the pattern of the patterned mask layer 120.

Figure 1C:
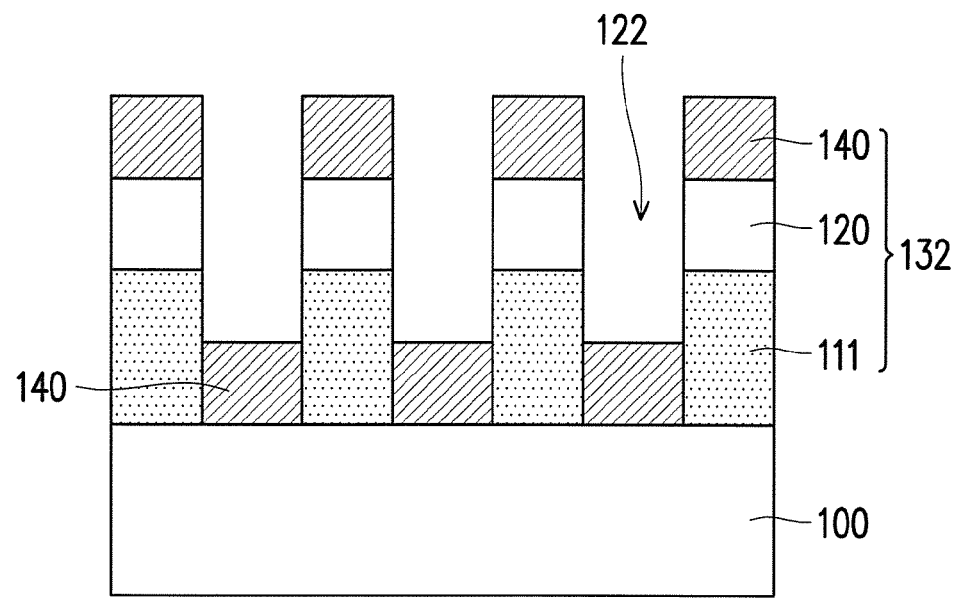

Then, referring to FIG. 1C, a metal material layer 140 is formed on each of the stacking structures 130 and on the substrate 100 located between two adjacent stacking structures 130. The stacking structures 130 and the metal material layer 140 disposed on the stacking structures 130 together form stacking structures 132. A method of forming the metal material layer 140 is an e-beam evaporation process, for example. The material of the metal material layer 140 is, for example, silver, gold, platinum, copper, aluminum, or a combination thereof, but the disclosure is not limited thereto. A thickness of the metal material layer 140 is from 10 nm to 100 nm, for example. According to the present embodiment, because heights of the patterned photoresist layer 111 and the patterned mask layer 120 are high enough (<140 nm), when the metal material layer 140 is formed, the metal material layer 140 deposited on the substrate 100 and the metal material layer 140 deposited on the patterned mask layer 120 are separated from each other.

Figure 1D:
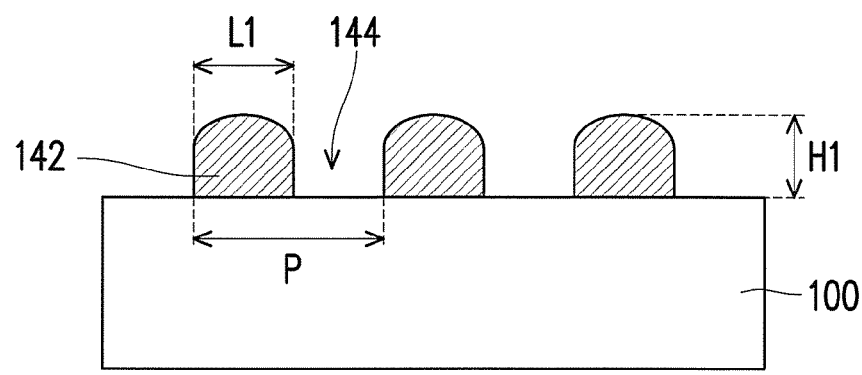

After that, each of the stacking structures 132 on the substrate 100 is removed. A method to remove the stacking structures 132 includes performing a wet stripping method, a dry stripping method, or a combination thereof. To be more specific, while the photoresist layer 111 is removed by the wet stripping method or the dry stripping method, the patterned mask layer 120 and the metal material layer 140 that are located on the photoresist layer 111 are also stripped off. Next, as shown in FIG. 1D, the metal material layer 140 on the substrate 100 is formed into a plurality of metal nanostructures 142 by a thermal annealing process. According to the present embodiment, openings 144 exist between two adjacent metal nanostructures 142, and the openings 144 expose a portion of the substrate 100. A size L1 of the metal nanostructures 142 is between 10 nm and 900 nm, for example. A height H1 of the metal nanostructures 142 is between 10 nm and 100 nm, for example.

In the present embodiment, as shown in FIG. 1C and FIG. 1D, the openings 122 of the patterned mask layer 120 are periodically and regularly distributed. Therefore, a location of each of the openings 122 is respectively corresponding to a location of each of the metal nanostructures 142. In other words, the metal nanostructures 142 are periodically and regularly arranged on the substrate 100, and a position pattern that the metal nanostructures 142 are arranged are corresponding to the openings 122. A period P of the metal nanostructures 142 is, for example, between 15 nm and 1000 nm, wherein P>L1. The periodically arranged structures have an advantage of high uniformity, that signal strength won't be impacted due to a change of measuring position. In addition, in the present embodiment, the shape of the metal nanostructures 142 is semi-spherical shape (as shown in FIG. 1D). In other embodiments, a shape of the metal nanostructures 142 may have cylindrical shape, disc shape, moth-eye shape, triangular-prism shape, or a combination thereof, but the disclosure is not limited thereto, a person of ordinary skill in the art can change the shape of the metal nanostructures according to requirements.

Figure 1E:
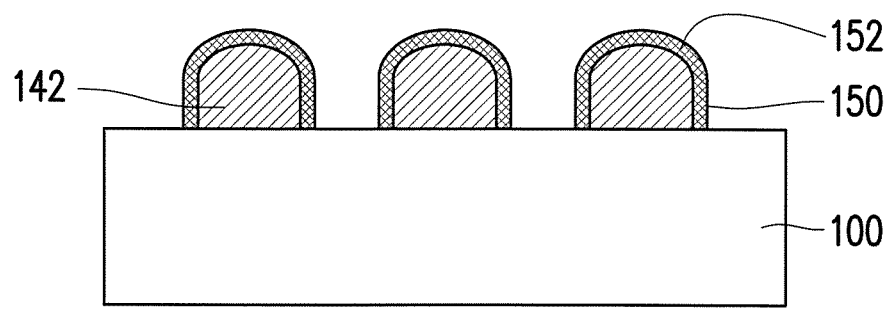

Thereafter, referring to FIG. 1E, a surface modified layer 150 is formed on a surface of the metal nanostructures 142, and is used to capture the antibody or aptamer corresponding to the analyte molecules (such as virus, antigen or protein). The surface modified layer 150 includes a plurality of thiol group-containing molecules 152. The thiol group-containing molecules 152 are, for example, 11-mercaptoundecanoic acid (11-MUA), 11-amino-1-undecanethiol (11-AUT), cysteamine, 4-aminothiophenol, 4-methylthiophenol, thiolated aptamer, or a combination thereof. A method of forming the surface modified layer 150 is, for example, immersing the entire structure as shown in FIG. 1D into a solution having the aforesaid chemical compounds. Of immersion process, one end of thiol group of the thiol group-containing molecules 152 is reacted with metal located on the surface of the metal nanostructures 142, so as to form covalent bonds.

Although the surface modified layer 150 is in contact with a part of the substrate 100 as shown in FIG. 1E, the structure shown in FIG. 1E is merely used as an exemplary example. That is, in the present embodiment, the thiol group-containing molecules 152 merely react with metal and do not react with the substrate 100, and thus the surface modified layer 150 is merely formed on the surface of the metal nanostructures 142, but not formed on the surface of the substrate 100. The surface modified layer 150 depicted in FIG. 1E is a schematic view, and since the surface modified layer 150 and the substrate 100 are not able to have reactions, the molecules of the surface modified layer 150 are, in fact, not formed on the surface of the substrate 100.

In addition, in the present embodiment, the antibody or aptamer corresponding to the analyte molecules is effectively conjugated with the surface modified layer 150, so as to increase the probability that the analyte molecules are immobilized on an effective sensing area, thereby increasing the sensitivity level of the sensing chip.

Figure 1F:
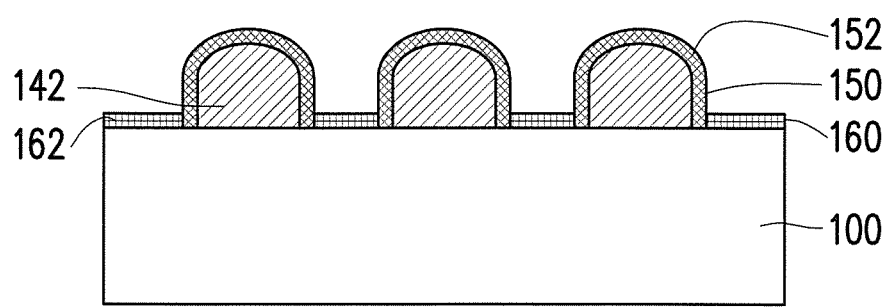

Thereafter, referring to FIG. 1F, a surface modified layer 160 is formed on the surface of the substrate 100 and used to resist sticking the analyte molecules. The surface modified layer 160 includes a plurality of silyl group-containing molecules 162. The silyl group-containing molecules 162 are, for example, poly(ethylene glycol)-silane (PEG-silane), polyvinylpyrrolidone-silane (PVP-silane), polyethyleneoxide-silane (PEO-silane), or combinations thereof. The method of forming the surface modified layer 160 is, for example, immersing the entire structure as shown in FIG. 1E into a solution having the aforesaid chemical compounds. Of immersion process, the silyl group of the silyl group-containing molecules 162 is reacted with silicone dioxide on the surface of the substrate 100, so as to form covalent bonds. Here, the manufacturing process of the sensing chip 10 is completed.

In the present embodiment, the silyl group-containing molecules 162 merely react with the substrate 100 and do not react with the metal nanostructures 142, and thus the surface modified layer 160 is formed on the surface of the substrate 100, but not formed on the surface of the metal nanostructures 142. Similarly, the surface modified layer 160 depicted in FIG. 1F is a schematic view, and since the surface modified layer 160 and the metal nanostructures 142 are not able to have reactions, the molecules of the surface modified layer 160 are, in fact, not formed on the surface of the metal nano structures 142.

In the present embodiment, the surface modified layer 160 is able to effectively inhibit the analyte molecules (such as antigen or protein) sticking onto the surface of the substrate 100, so as to reduce noise interference generated by non-specific binding of the analyte molecules and to increase the probability that the analyte molecules are immobilized on the effective sensing area, and thereby increasing sensitivity level and accuracy of the sensing chip.

Figure 2A:
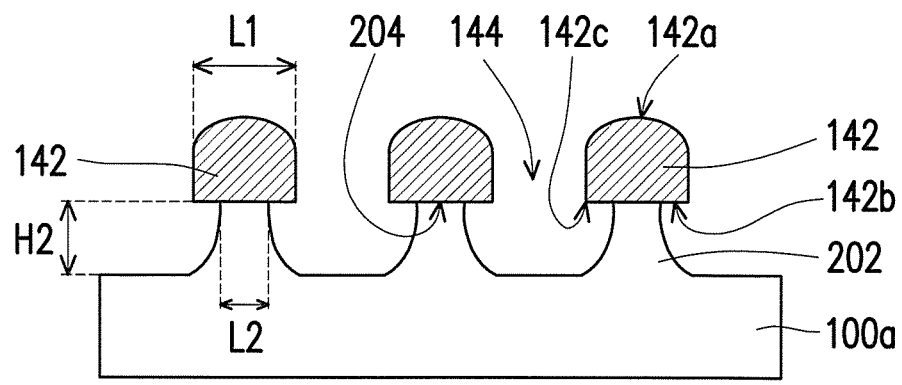
FIGS. 2A to 2C are schematic cross-sectional views depicting a manufacturing process of a sensing chip according to a second embodiment of the disclosure.
Figure 2B:
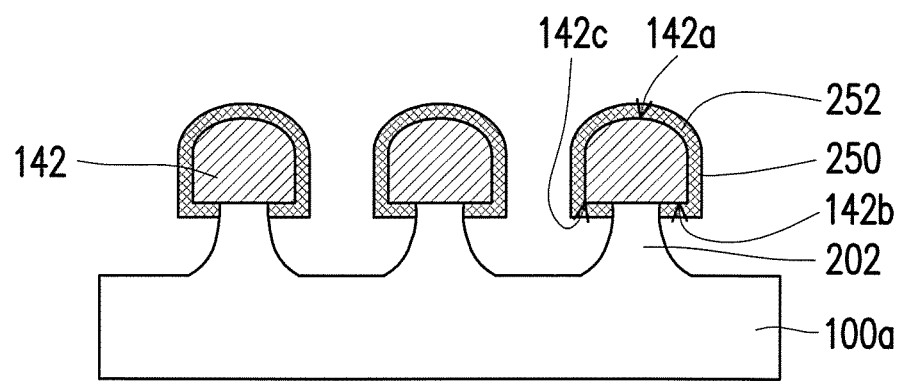
Figure 2C:
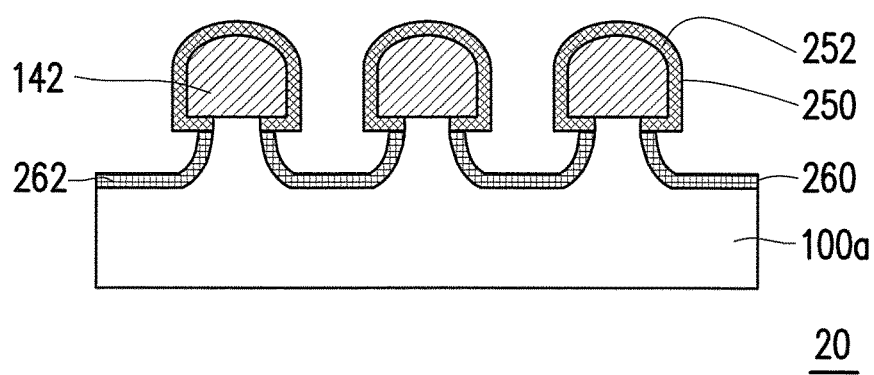

FIGS. 2A to 2C are schematic cross-sectional views depicting a manufacturing process of a sensing chip according to a second embodiment of the disclosure. It should be noted here, a part of the manufacturing process of the aforementioned embodiment (the first embodiment) is applied to the following embodiment (the second embodiment), where the following subsequent manufacturing steps are performed after the FIG. 1D. In the following embodiments, the same reference numbers and a portion of the contents from the previous embodiment are used, wherein the same reference numbers are used in the drawings and the description to refer to the same or like parts, and the similar technical content will be omitted. The details of the omitted parts can be referring to the previous embodiment, and will not be repeated herein.

Referring to FIG. 2A, after forming the metal nanostructures 142 as shown in FIG. 1D, the metal nanostructures 142 serve as an etching mask, and a wet etching process (e.g., using HF or KOH aqueous solution) is performed on the substrate 100 to form a substrate 100a and a plurality of supporting structures 202 located on the substrate 100a. The supporting structures 202 are located between the substrate 100a and the metal nanostructures 142, so that the metal nanostructures 142 is spaced from the substrate 100a by a distance. In the present embodiment, an etch depth of the wet etching process is approximately the same as a height H2 of the supporting structures 202, and thus the height of the supporting structures is controlled by controlling the etching time. The height H2 of the supporting structures 202 is between 10 nm and 100 nm, for example.

In the present embodiment, each of the metal nanostructures 142 has an upper surface 142a and a lower surface 142b. In the present embodiment, the upper surface 142a is an arc surface, but the disclosure is not limited thereto. The lower surface 142b has a corner area 142c. The lower surface 142b and the supporting structure 202 have a contact surface 204 therebetween. The wet etching method is an isotropic etching; therefore, while the wet etching process is performed, not only the part of the substrate 100 exposed by the openings 144 is etched away, but a part of the substrate 100 under the metal nanostructures 142 is also laterally etched. Such that, a width L2 of the contact surface 204 is smaller than the width L1 of the metal nanostructures 142.

Subsequently, referring to FIG. 2B, a surface modified layer 250 is formed on the surface of the metal nanostructures 142, and is used to capture the antibody or aptamer corresponding to the analyte molecules. The surface modified layer 250 includes a plurality of thiol group-containing molecules 252. The thiol group-containing molecules 252 are, for example, 11-mercaptoundecanoic acid (11-MUA), 11-amino-1-undecanethiol (11-AUT), cysteamine, 4-aminothiophenol, 4-methylthiophenol, thiolated aptamer, or combination thereof. A method of forming the surface modified layer 250 is, for example, immersing the entire structure as shown in FIG. 2A into a solution having the aforesaid chemical compounds. Of immersion process, one end of thiol group of the thiol group-containing molecules 252 and is reacted with metal located on the upper surface 142a, the lower surface 142b and the corner area 142c of the metal nanostructures 142, so as to form covalent bonds.

Although the surface modified layer 250 is in contact with a part of the supporting structures 202 as shown in FIG. 2B, the structure shown in FIG. 2B is merely used as an exemplary example. That is, in the present embodiment, the thiol group-containing molecules 252 merely react with metal and do not react with the supporting structures 202 and the substrate 100a, and thus the surface modified layer 250 is merely formed on the upper surface 142a, the lower surface 142b and the corner area 142c of the metal nanostructures 142, but not formed on the surface of the supporting structures 202 and the substrate 100a.

In addition, in the present embodiment, the antibody or aptamer corresponding to the analyte molecules (such as antigen or protein) is effectively conjugated with the surface modified layer 250, so as to increase the probability that the analyte molecules are immobilized on an effective sensing area, thereby increasing the sensitivity level of the sensing chip.

In the present embodiment, because the supporting structures 202 are located between the substrate 100a and the metal nanostructures 142, the metal nanostructures 142 and the substrate 100a are spaced away by a distance. Thus the sensing hot spot located at a junction of the corner area 142c of the metal nanostructures 142 and the substrate 100a is shifted upward from the substrate 100a, and which is beneficial to the analyte molecules approaching from all directions, since the impact of the steric hindrance is reduced when immobilizing. In addition, the lateral etching effect of the wet etching process may hollow the substrate located under the sensing hot spot, so that the sensing hot spot is more exposed to the surrounding environment and thereby increasing the sensitivity level of the sensing chip.

After that, referring to FIG. 2C, a surface modified layer 260 is formed on the surfaces of the substrate 100a and the supporting structures 202, and is used to resist sticking the analyte molecules. The surface modified layer 260 includes a plurality of silyl group-containing molecules 262. The silyl group-containing molecules 262 are, for example, poly (ethylene glycol)-silane (PEG-silane), polyvinylpyrrolidone-silane (PVP-silane), polyethyleneoxide-silane (PEO-silane), or combinations thereof. The method of forming the surface modified layer 260 is, for example, immersing the entire structure as shown in FIG. 2B into solution having the aforesaid chemical compounds. Of immersion process, the silyl group of the silyl group-containing molecules 262 is reacted with silicone dioxide on the surfaces of the substrate 100a and the supporting structures 202, so as to form covalent bonds. Here, the manufacturing process of the sensing chip 20 is completed.

In the present embodiment, the surface modified layer 260 is able to effectively inhibit the analyte molecules (such as antigen or protein) sticking onto the surfaces of the substrate 100a and the supporting structures 202, so as to reduce noise interference generated by non-specific binding of the analyte molecules and to increase the probability that the analyte molecules are immobilized on the effective sensing area, and thereby increasing sensitivity level and accuracy of the sensing chip.

In the following, embodiments of the disclosure are taken as exemplary examples to describe the disclosure more specifically. However, without departing from spirit of the disclosure, the material, the usage method and so forth, of the following embodiments may be appropriately changed. Therefore, scope of the disclosure should not be interpreted as limited to the following embodiments.

[Experiment of Structural Designs of a LSPR Sensing Chip]

In the present embodiment, a finite-difference-time-domain (FDTD) method is used to analyze simulation structures 1-3. The simulation structure 1 has the structure shown in FIG. 2A, wherein a material of the metal nanostructures is gold; the simulation structure 2 has the structure shown in FIG. 1D, wherein the material of the metal nanostructures is gold; the simulation structure 3 is similar to the simulation structure 2, the difference is that the metal nanostructures of the simulation structure 3 are a multi-layered metal nanostructures which is sandwiched alumina by gold (e.g., a multi-layered structure of gold-alumina-gold).

Table 1 shows sensitivity level and process yield of the simulation structures 1-3 after analyzing by the FDTD method. As shown in Table 1, sensitivity levels of the simulation structure 1, the simulation structure 2, and the simulation structure 3 are 331 nm/RIU, 230 nm/RIU, and 280 nm/RIU, respectively. Based on the above results, the simulation structure 1 has the highest sensitivity level and a high process yield, therefore, the simulation structure 1 is suitable to serve as LSPR chip structure.

TABLE 1

|  | Sensitivity level (nm/RIU) | Process yield |
|---|---|---|
| Simulation structure 1 | 331 | High |
| Simulation structure 2 | 230 | High |
| Simulation structure 3 | 280 | Low |

[Experiment of Sensitivity Level of a LSPR Sensing Chip]

Embodiment 1

The embodiment 1 is the sensing chip structure as shown in FIG. 2A (e.g., performing a wet etching process on the substrate).

Figure 3:
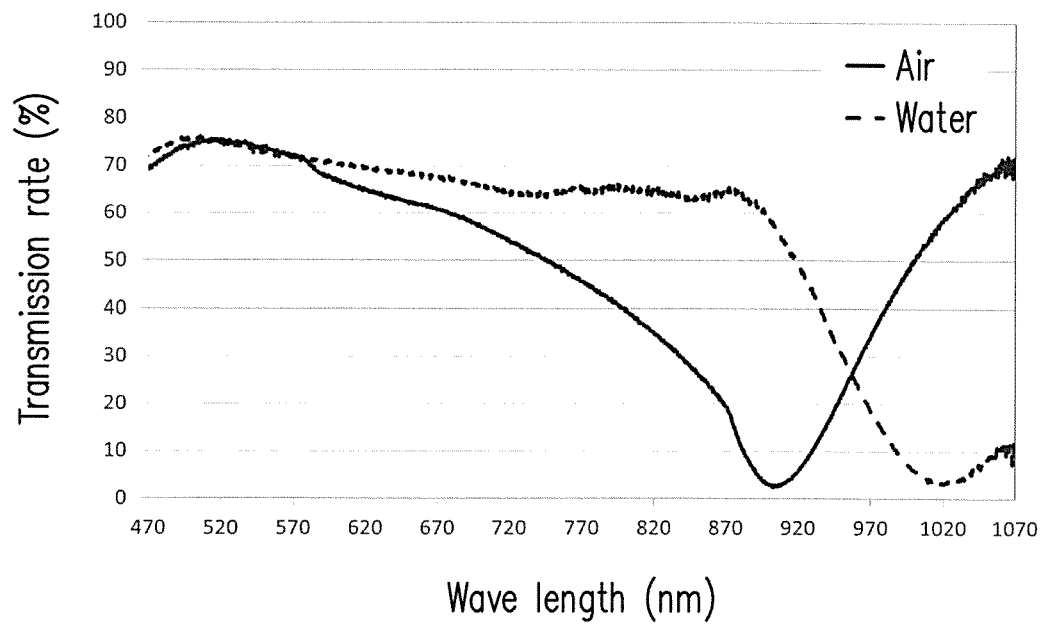
FIG. 3 is a graph of the characteristic spectra of a sensing chip of an embodiment 1 in air and in water.

The sensing chip of the embodiment 1 was respectively placed in the air (a refractive index is 1.0) and in water (a refractive index is 1.33), and a sensitivity level of the sensing chip was estimated by measuring a LSPR characteristic spectra of the sensing chip. FIG. 3 is a graph of the characteristic spectra of the sensing chip of the embodiment 1 in air and in water. As shown in FIG. 3, as the sensing chip of the embodiment 1 is moved from the air of a lower refractive index into water of a higher refractive index, the characteristic spectra of the sensing chip undergoes a 117 nm of red shift due to a high refractive index of the media. Thus, a sensitivity level of the sensing chip is about 351 nm/RIU by calculations.

Comparative Example 1

The comparative example 1 is the sensing chip structure as shown in FIG. 1D (e.g., not performing a wet etching process on the substrate).

Figure 4:
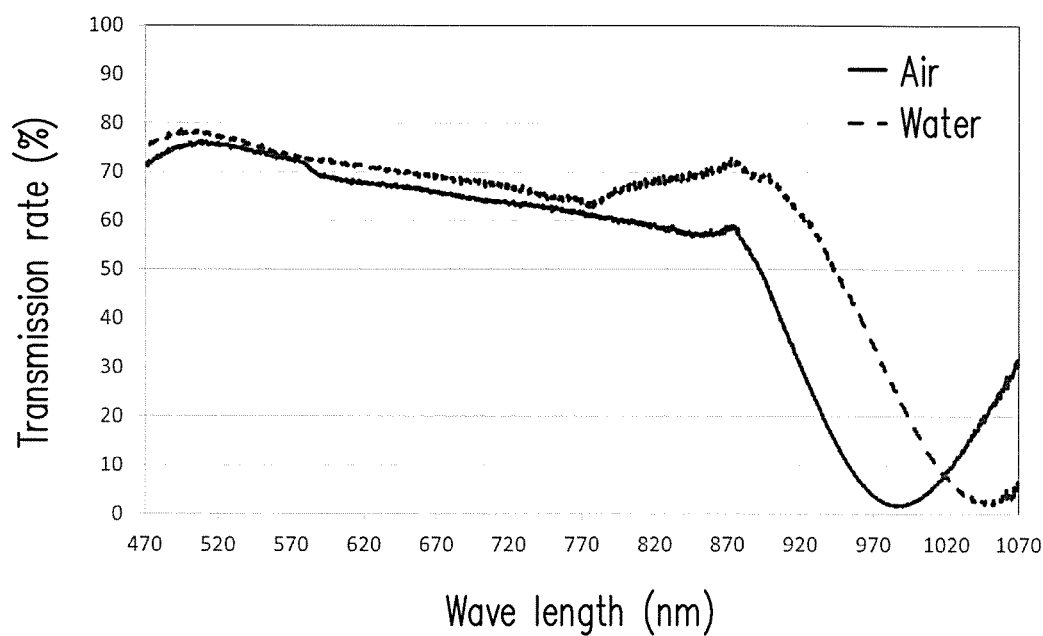
FIG. 4 is a graph of the characteristic spectra of a sensing chip of a comparative example 1 in air and in water.

The sensing chip of the comparative example 1 was respectively placed in air (the refractive index is 1.0) and in water (the refractive index is 1.33), and a sensitivity level of the sensing chip was estimated by measuring a LSPR characteristic spectra of the sensing chip. FIG. 4 is a graph of the characteristic spectra of the sensing chip of the comparative example 1 in the air and in water. As shown in FIG. 4, as the sensing chip of the comparative example 1 is moved from the air of the lower refractive index into water of the higher refractive index, the characteristic spectra of the sensing chip undergoes a 63 nm of red shift due to a high refractive index of the media. Thus, a sensitivity level of the sensing chip is 189 nm/RIU by calculations.

Based on the results above, the embodiment 1 has a higher sensitivity level as compared with the comparative example 1.

Figure 5A:
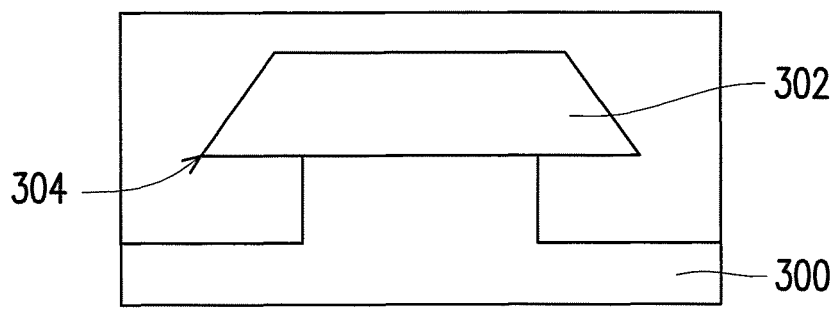
FIG. 5A is a diagram of a FDTD simulation result of a distribution of energy hot spots of the embodiment 1.
Figure 5B:
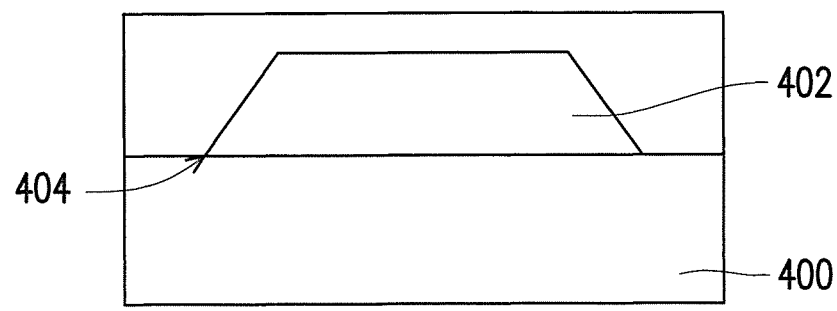
FIG. 5B is a diagram of a FDTD simulation result of a distribution of energy hot spots of the comparative example 1.

FIG. 5A is a diagram of a FDTD simulation result of a distribution of energy hot spots of the embodiment 1. FIG. 5B is a diagram of a FDTD simulation result of a distribution of energy hot spots of the comparative example 1. Compared to a sensing hot spot 404 of the comparative example 1 located at a junction between a substrate 400 and a metal nanostructure 402, a metal nanostructure 302 and the substrate 300 of the embodiment 1 are spaced apart by a distance, so that a sensing hot spot 304 of the embodiment 1 is exposed, and it is beneficial to the analyte molecules that are approaching the sensing hot spot of the embodiment 1 in all directions.

[Effect of Etching Depth to Sensitivity Level]

Figure 6:
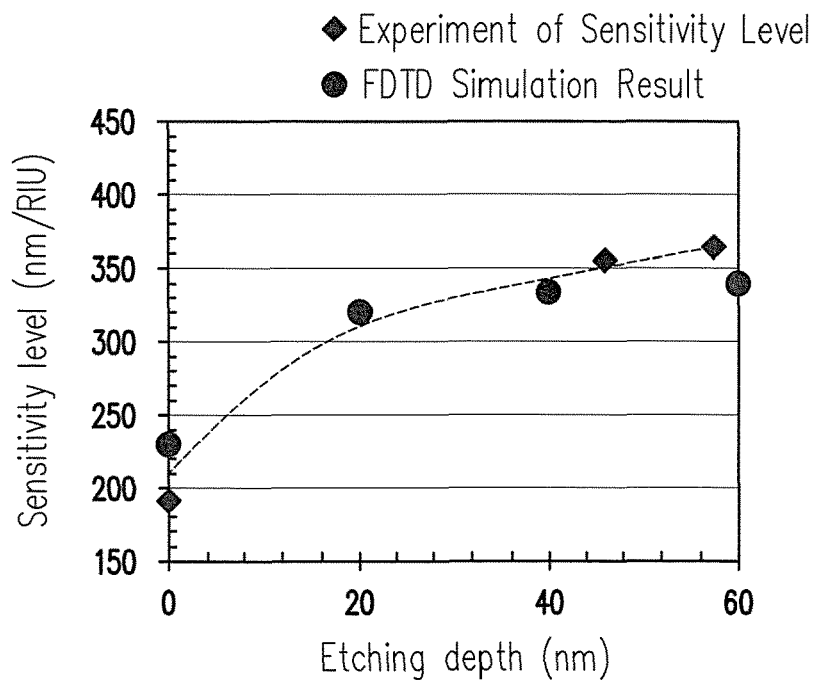
FIG. 6 is a comparison chart of experimental sensitivity level and FDTD simulation result.

Because the etching time is corresponding to the etching depth, and in order to test the sensitivity level of the sensing chips having different etching depths, wet etching processes with different etching times are respectively performed on the sensing chip shown in FIG. 1D, and a sensitivity level of the sensing chips manufactured with the different etching times is measured. In addition, the results obtained above and corresponding FDTD simulation resulted are superposed. FIG. 6 is a comparison chart of the experimental sensitivity level results and a FDTD simulation result. Tendencies of the experimental sensitivity level and the FDTD simulation result are matched, as indicated in FIG. 6. When the etching depth is deeper, the sensitivity level of the sensing chip manufactured becomes higher. This phenomenon may be explained by the location of the sensing hot spot of the sensing chip. When the etching depth is zero (the structure as shown in FIG. 1D), the sensing hot spot is located at the junction of the metal nanostructure and the substrate, therefore, most of energy is buried in the substrate, thereby lowering the sensitivity level of the sensing chip. However, with the increment of the etching time (e.g., increasing the etching depth and the lateral etching level), a distance between the sensing hot spot and the substrate is increased, such that the sensing hot spot is more exposed to the surrounding environment, therefore, the sensitivity level of the sensing chip becomes higher.

[Test for Biotin-Avidin System]

In order to test the LSPR sensing chip manufactured in the disclosure on biological samples so as to obtain actual test results, in the present embodiment, a biotin-avidin system having high specificity and high affinity is used to conduct experiment, wherein a selected biotin is NH2-PEG4-biotin, a selected avidin is NeutrAvidin. NeutrAvidin is a modified avidin that is deglycosylated, and which is barely capable of sticking.

Embodiment 2 (Performing Two-Stage Surface Modification)

First, the sensing chip as shown in FIG. 1D was immersed in a 0.1 mM 11-amino-1-undecanethiol (11-AUT) solution for 24 hours to perform a first stage surface modification. Next, the sensing chip was immersed in a 6 mM 2-[Methoxy (polyethyleneoxy)propyl]trimethoxysilane (m-PEG silane) solution, and then was heated at 60° C. to react for 24 hours under a nitrogen environment to perform a second stage surface modification. After that, the sensing chip was immersed in a 0.25% glutaraldehyde (GTA) solution. In this step process, one end of an aldehyde group of glutaraldehyde and an amino group of 11-AUT formed a covalent bond. Then, a 1 mM NH2-PEG4-biotin solution was dripped on the sensing chip and shook for half an hour; and in this step process, another end of the aldehyde group of glutaraldehyde and the amino group of NH2-PEG4-biotin formed a covalent bond. Subsequently, the sensing chip was cleaned by a phosphate buffer solution, and NeutrAvidin solutions having different concentrations (0.5 μg/mL, 5 μg/mL, 50 μg/mL, 500 μg/mL) were dripped on the sensing chip and shook for half an hour. In this step process, NH2-PEG4-biotin and NeutrAvidin will have specific binding.

Comparative Example 2 (Performing One Stage Surface Modification)

A method similar to the method of the embodiment 2 was employed, and the difference was that the first stage (11-AUT) surface modification was performed on the sensing chip of the comparative example 2, and the second stage (m-PEG silane) surface modification was not performed.

Figure 7:
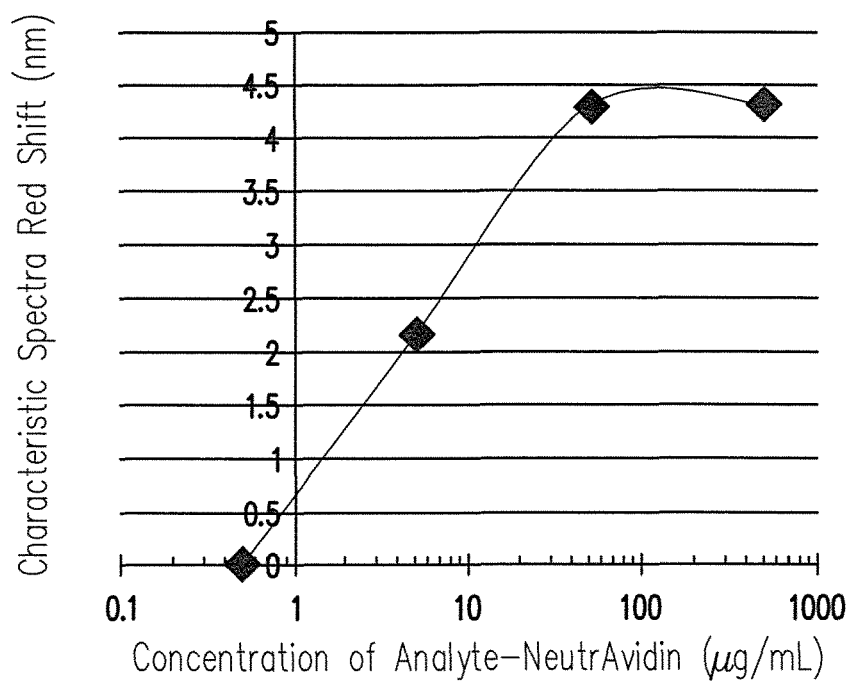
FIG. 7 is a relationship diagram of concentrations of analyte molecules in an embodiment 2 and corresponding characteristic spectra red shift.
Figure 8:
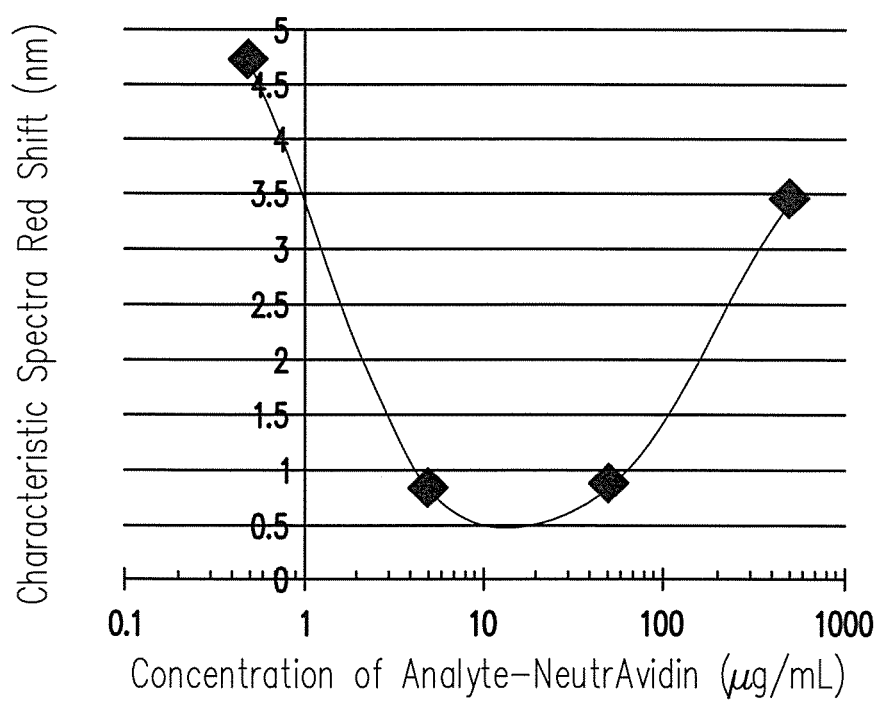
FIG. 8 is a relationship diagram of concentrations of analyte molecules in a comparative example 2 and characteristic spectra red shift.

FIG. 7 is a relationship diagram of concentrations of the analyte molecules in the embodiment 2 and characteristic spectra red shift. FIG. 8 is a relationship diagram of concentrations of the analyte molecules in the comparative example 2 and characteristic spectra red shift.

Referring to FIG. 7, when the concentration is in a range of 0.5~50 µg/mL, by the increment of the concentration of analyte molecules (NeutrAvidin), the characteristic spectra red shift is also increased. In other words, the relationship between the concentration of the analyte molecules and the characteristic spectra red shift (may be corresponding to signal strength) is a linear relationship. Such linear relationship becomes convergent, since the concentration of the analyte molecules exceeds 50 µg/mL, the surface of the sensing chip is fully covered by the analyte molecules and then reaches a saturated status, so that the spectral change become slower.

Referring to FIG. 8, by the increment of the concentration of the analyte molecules, the characteristic spectra red shift is not increased consequently. In other words, the relationship between the concentration of the analyte molecules and the characteristic spectra red shift is not a linear relationship.

Figure 9A:
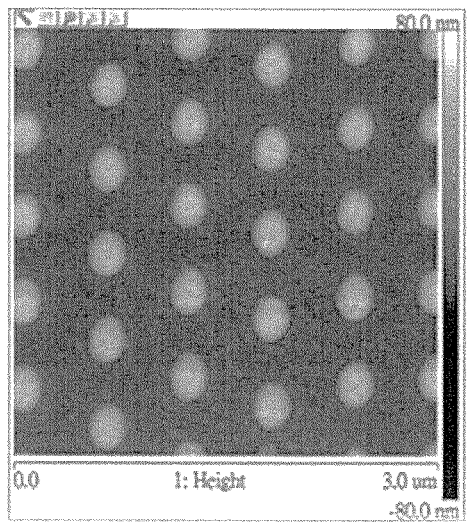
FIG. 9A is an atomic force microscope image of the embodiment 2.
Figure 9B:
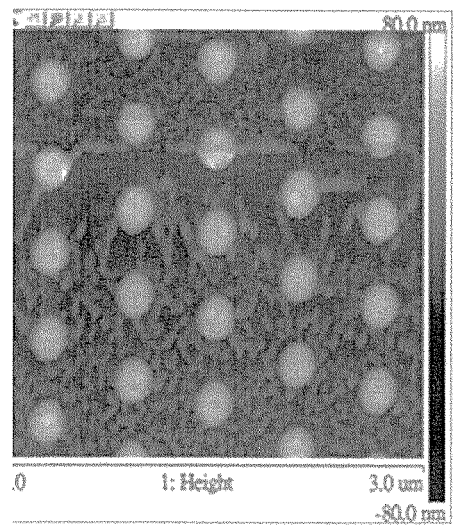
FIG. 9B is an atomic force microscope image of the comparative example 2.

FIG. 9A is an atomic force microscope image of the embodiment 2. FIG. 9B is an atomic force microscope image of the comparative example 2. Referring to FIGS. 9A and 9B simultaneously, after the sensing chip conjugates the analyte molecules (such as NeutrAvidin), there are many analyte molecules have been attracted onto an upper surface of a glass substrate of the sensing chip, which does not undergo the two-stage surface modification (e.g., the comparative example 2), and then form aggregations, as shown in the atomic force microscope (AFM) images. The surface roughness (Rq) of the upper surface of the glass substrate of the sensing chip is 6.7 nm. Therefore, it can be seen that a large amount of the analyte molecules has been vanished, which affects the linear relationship of the concentration measurement. In comparison, considering the sensing chip having the two-stage surface modification (e.g., the embodiment 2), a much less amount of the analyte molecules has been stuck onto the glass substrate, and thus a surface roughness (Rq) of the upper surface of the glass substrate is 2.3 nm. Therefore, in theoretically speaking, there will be no loss of the analyte molecules, which allows the most of the analyte molecules to be conjugated with the metal nanostructures, thereby increasing stability and reproducibility of the measuring system.

Based on the above results, the sensing chip of the disclosure undergoes the two-stage surface modification to prevent the analyte molecules sticking onto the non-sensing area, so as to increase the probability that the analyte molecules being conjugated to the sensing area, thereby enhancing the linear relationship between the concentration of the analyte molecules and the signal strength.

In light of the foregoing, the metal nanostructures and the substrate of the sensing chip are spaced apart by a distance, so that the sensing hot spot is exposed and is away from the substrate, thereby having a higher sensitivity level. In addition, the sensing chip of the disclosure undergoes the two-stages surface modification, which not only increases the probability that the analyte molecules being conjugated on the effective sensing area, but also reduces the noise interference generated by the analyte molecules sticking on the non-sensing area, thereby enhancing the linear relationship between the signal strength and the concentrations of the analyte molecules, and increasing sensitivity level of the sensing chip.

It will be apparent to those skilled in the art that various modifications and variations can be made to the structure of the disclosed embodiments without departing from the scope or spirit of the disclosure. In view of the foregoing, it is intended that the disclosure cover modifications and variations of this disclosure provided they fall within the scope of the following claims and their equivalents.

What is claimed is:

1. A sensing chip, comprising:
    a substrate;
    a plurality of metal nanostructures, disposed on the substrate;
    a first surface modified layer, disposed on surfaces of the metal nanostructures, wherein the first surface modified layer comprises a plurality of thiol group-containing molecules;
    a second surface modified layer, disposed on a surface of the substrate, wherein the second surface modified layer comprises a plurality of silyl group-containing molecules; and
    a plurality of supporting structures located between the substrate and each of the metal nanostructures, so that each of the metal nanostructures is spaced from the substrate by a distance,
    wherein each of the metal nanostructures has an upper surface and a lower surface, and the lower surface and one of the supporting structures have a contact surface therebetween,
    wherein a width of the contact surface is smaller than a width of each of metal nanostructures, and
    wherein a width of each of the plurality of supporting structures is gradually decreased along a direction from the substrate towards the plurality of metal nanostructures.

2. The sensing chip as claimed in claim 1, wherein: the first surface modified layer is located on the surfaces of the metal nanostructures and is not located on the surface of the substrate, and the second surface modified layer is located on the surface of the substrate and is not located on the metal nanostructures.

3. The sensing chip as claimed in claim 1, wherein a height of each of the supporting structures is from 10 nm to 100 nm.

4. The sensing chip as claimed in claim 1, wherein: the lower surface has a corner area, and the thiol group-containing molecules of the first surface modified layer are immobilized on the upper surface of the metal nanostructures, the lower surface, and the corner area.

5. The sensing chip as claimed in claim 1, wherein the second surface modified layer is located on surfaces of each supporting structure and the substrate.

6. The sensing chip as claimed in claim 1, wherein a material of the supporting structures and a material of the substrate are the same.

7. The sensing chip as claimed in claim 1, wherein a size of the metal nanostructures is between 10 nm and 900 nm.

8. The sensing chip as claimed in claim 1, wherein a height of the metal nanostructures is between 10 nm and 100 nm.

9. The sensing chip as claimed in claim 1, wherein the metal nanostructures are periodically and regularly arranged on the substrate, a period of the metal nanostructures is between 15 nm and 1000 nm.

10. The sensing chip as claimed in claim 1, wherein a shape of the metal nanostructures comprises cylindrical shape, semi-spherical shape, disc shape, moth-eye shape, triangular prism shape, or a combination thereof.

11. The sensing chip as claimed in claim 1, wherein a material of the metal nanostructures comprises silver, gold, platinum, copper, aluminum, or a combination thereof.

12. The sensing chip as claimed in claim 1, wherein the thiol group-containing molecules comprise 11-mercaptoundecanoic acid, 11-amino-1-undecanethiol, cysteamine, 4-aminothiophenol, 4-methylthiophenol, thiolated aptamer, or a combination thereof.

13. The sensing chip as claimed in claim 1, wherein the silyl group-containing molecules comprise poly(ethylene glycol)-silane, polyvinylpyrrolidone-silane, polyethylene-oxide-silane, or a combination thereof.

* * * * *